United States Patent [19]

Neti et al.

[11] 4,002,547
[45] Jan. 11, 1977

[54] ELECTROCHEMICAL REFERENCE ELECTRODE

[75] Inventors: Radhakrishna M. Neti, Brea; Colin C. Bing, Placentia, both of Calif.

[73] Assignee: Beckman Instruments, Inc., Fullerton, Calif.

[22] Filed: July 22, 1974

[21] Appl. No.: 490,544

Related U.S. Application Data

[63] Continuation of Ser. No. 65,898, Aug. 21, 1970, abandoned, which is a continuation-in-part of Ser. No. 818,935, April 24, 1969, abandoned.

[52] U.S. Cl. ............................ 204/195 F; 204/296; 260/42.27
[51] Int. Cl.² .................. G01N 27/40; G01N 27/46
[58] Field of Search .......... 204/195 F, 195 M, 1 T, 204/296; 260/92.1 S

[56] References Cited
UNITED STATES PATENTS

| | | | |
|---|---|---|---|
| 2,400,099 | 5/1946 | Brubaker et al. | 260/92.1 S |
| 3,438,875 | 4/1969 | Watanabe et al. | 204/195 F |
| 3,590,810 | 7/1971 | Kopecky | 204/195 M |
| 3,728,303 | 4/1973 | Kometani et al. | 260/92.1 S |

OTHER PUBLICATIONS

Buchanan et al., "Analytical Chemistry", vol. 40, No. 3, Mar. 1968, pp. 517–521.

*Primary Examiner*—T. Tung
*Attorney, Agent, or Firm*—Robert J. Steinmeyer; Donald A. Streck

[57] ABSTRACT

An electrochemical reference electrode for use in ion potential measurements of solutions. The liquid junction structure of the electrode comprises a hydrophobic polymer having a suitable salt distributed therethrough and held in place to prevent leaching by a filamentary structure of the polymer. The liquid junction structure is a diffusion membrane material and permits ionic communication between the salt bridge solution of the electrode and the sample solution essentially by means of diffusion, rather than by liquid flow. The entire electrode body may be made of the polymeric material. The electrode is particularly suited for process applications.

4 Claims, 8 Drawing Figures

INVENTORS
RADHAKRISHNA M. NETI
COLIN C. BING

BY William F. McDonald
ATTORNEY

INVENTORS
RADHAKRISHNA M. NETI
COLIN C. BING
BY
*William F. McDonald*
ATTORNEY

ELECTROCHEMICAL REFERENCE ELECTRODE

CROSS-REFERENCE TO RELATED APPLICATIONS

This is a continuation of application Ser. No. 65,898 filed Aug. 21, 1970, now abandoned, which is in turn a continuation-in-part of application Ser. No. 818,935, filed Apr. 24, 1969, also abandoned.

BACKGROUND OF THE INVENTION

1. Field of the Invention

This invention relates generally to an electrochemical reference electrode and, particularly, to a diffusion membrane material useful as a liquid junction structure of a salt bridge tube such as is used in reference electrodes for ion potential measurements of solutions.

2. Description of the Prior Art

In making measurements of the ion concentration of solutions, a reference electrode is commonly employed in conjunction with a sensing electrode, such as a glass electrode, with both electrodes immersed in the test solution. The potential difference between the two electrodes is a function of the concentration of a specific ion in the solution. A typical example is the conventional pH meter and electrode pair used for measuring hydrogen ion concentrations of solutions.

A reference electrode ordinarily comprises an internal half cell supported in a tube containing a salt solution, the tube of salt solution being known as a salt bridge. The salt bridge solution is a strong equitransferent salt solution such as saturated potassium chloride or potassium nitrate. Electrical connection between the salt solution and the sample or test solution is made by liquid flow through a suitably formed aperture or passage in the tube, generally referred to as a liquid junction structure or leak structure. Sometimes the entire unit consisting of the internal half cell structure, the tube, the salt solution and the liquid junction structure is referred to as a half cell; however, for the present specification, the entire unit will be referred to as a reference electrode.

Various means have been utilized for forming the liquid junction structures of salt bridge tubes, including agar gel connections, wicking, asbestos fibers, small capillary tubes, glass tubes with cracks therein, sintered glass plugs sealed in glass tubes, annular passages provided between solid metal rods and the walls of the tubes, porous ceramic rods, porons sintered plastic rods, and ground glass sleeves.

The liquid junction behavior must be substantially independent of the character of the test solution and thus give substantially reproducible potentials. Although the structures referred to above generally satisfy this requirement, they have one or more objectionable features including slow and costly methods of manufacture, high rate of flow of salt solution, lack of uniformity in flow rates and electrical resistance with like liquid junction structures, and lack of durability.

The above mentioned liquid junction structures have two primary disadvantages when utilized in process applications wherein the electrodes must be disposed in high pressure process streams containing viscous liquids. One of these disadvantages is the requirement of an external pressurization of the salt bridge solution in the reference electrode in order to assure that there is a flow of salt bridge solution from the electrode into the sample so that electrical contact will be maintained during the analysis of the sample. Otherwise sample will migrate into the salt bridge solution contaminating the same and also the internal half cell, thus resulting in sparious potentials being developed. The second disadvantage of such liquid junction structures is that they become clogged in many process streams due to viscous substances contained therein, such as molasses, clay slurries, gelatin mixtures, etc., thereby preventing the flow of salt solution from the reference electrode into the sample medium. When this occurs, the electrical connection between the two solutions ceases and the reference electrode is rendered inoperable. What is needed, therefore, is means for providing a liquid junction whose permeability to ions is based essentially upon diffusion, not liquid flow, and thus will not be subject materially to plugging or clogging by viscous liquids or passage of contaminating constituents therethrough from the sample into the salt bridge solution and further eliminating the need for pressurization equipment under normal use of the electrode.

One type of liquid junction structure meeting these requirements employs a naturally hydrophilic semipermeable membrane material, such as cellophane, collodion, cellulose acetate or protein membranes, which closes the open end of a salt bridge tube and is utilized in the analysis of biological fluids such as blood. While these membrane liquid junction structures are not clogged by biological liquids and ions pass therethrough by diffusion rather than liquid flow, they are not entirely satisfactory for process applications since the membranes may deform under varying pressure conditions of the process stream, thus altering the junction potential, and may become ruptured. Thus, what is desired is a liquid junction structure for a reference electrode which has the advantages of the above mentioned hydrophilic membrane liquid junction structures, and in addition is highly durable, has a reasonably low electrical resistance, does not require internal pressurization from an external pressure source and has a reasonably long life, on the order of several months without any attention by an operator. Also, the desired liquid junction structure should be capable of being steam sterilized, have a constant temperature coefficient between like structures and be insensitive to the flow of the sample medium.

SUMMARY OF THE INVENTION

It is an object of the present invention to provide an improved liquid junction structure for an electrochemical reference electrode assembly which has a permeability to ions that is based essentially upon diffusion, rather than capillary liquid flow.

Another object of the invention is to provide an improved liquid junction structure which meets most if not all of the desired characteristics discussed above.

Another object of the instant invention is to provide a diffusion membrane which, among other uses, may be used as the improved liquid junction structure.

According to the principal aspect of the present invention, there is provided a liquid junction structure for an electrochemical reference electrode assembly which permits the passage of ions essentially by diffusion and not by capillary action. In the preferred embodiment a relatively strong, electrochemically inactive salt is distributed throughout a hydrophobic polymer, such as polytetrafluoroethylene, so as to render the polymer a diffusion membrane material. The above-mentioned salt is incorporated in the polymer in order to lower the volume resistivity of the polymer so that when the polymer is formed as a liquid junction structure the resistance thereof will be in the normally desired range for performing ion potential measurements and the affect of any metallic impurities in the polymer will be masked. Liquid junction structures formed in accordance with the present invention are not subject to clogging, do not require external pressurization for use in process steam applications and are flow insensitive. In addition, the liquid junction structures of the invention embody the other desired characteristics discussed previously herein in connection with prior art liquid junction structures.

Other objects, aspects and advantages of the invention will become apparent from the following description taken is connection with the accompanying drawing.

DESCRIPTION OF THE PREFERRED EMBODIMENT

Figure 1:
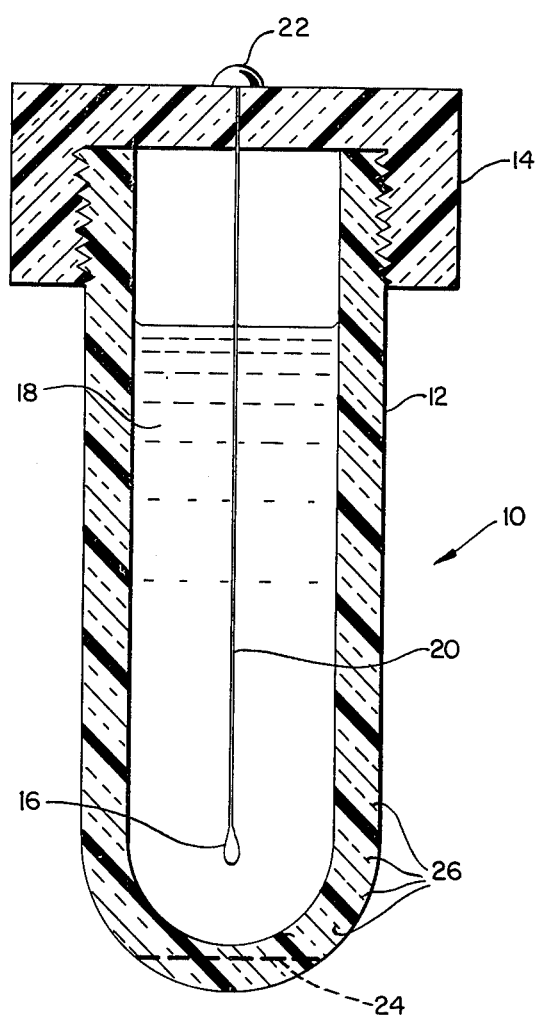
FIG. 1 illustrates on a somewhat enlarged scale the preferred form of the reference electrode of the present invention, in longitudinal section.

In one embodiment of the invention, the liquid junction structure is formed of a polymeric resin forming material, either a synthetic or a natural polymer, such as a plastic or rubber, which is capable of being hydrated. This requires that the polymer contain a hydrophilic group which includes, but is not limited to, aldehyde, phenol, amide, or carboxyl. Polymers containing these groups may be hydrated by treating them in an aqueous solution, either by soaking the polymers in the solution at room temperature or boiling the polymers in aqueous solution, preferably distilled water. According to prevailing theories, hydration of these polymers takes place by the formation of a hydrogen bond between the water molecule and the reactive or hydrophilic group. This causes the polymer to become more hydrophilic, whereby hydrogen and hydroxyl ions, and probably some other small ions, may pass through the polymer by means of diffusion rather than by liquid flow. Thus, in accordance with this aspect of the invention, a hydrateable polymeric material is hydrated so as to become more hydrophilic and thus permit ionic diffusion, but the hydration does not render the polymer porous so that liquid flow will occur.

By way of example, rubber materials containing hydrophilic groups, and hence which are hydrateable are silicone, butadiene and polyurethane while suitable plastics which have been successfully utilized to practice the present invention are nylon and acrylonitrile-butadiene-styrene. It is of course understood that other polymers containing hydrophilic groups may be utilized.

The above materials may be formed into a suitably shaped liquid junction structure, as for example, in the form of a disc which is sealed in the end of a salt bridge tube of a reference electrode. In the preferred embodiment of the invention, however, the preferred liquid junction material which will be discussed later herein is provided in the form of a bar stock which is machined to provide the entire electrochemical reference electrode body. Reference is made to the drawing in which an electrode so constructed is illustrated and is generally designated by numeral 10. The electrode comprises a cylindrical tube or container 12 which is closed at its lower end as shown. The upper end of the container is closed in any appropriate manner as by a cap 14 which is threadedly engaged onto the container. An internal half cell 16 is disposed in a body of suitable strong, equitransferent salt bridge solution 18, such as saturated potassium chloride, in the container. The half cell 16 is connected by means of a conductor 20 to a terminal 22 on the external surface of the cap 14. This terminal is adapted to be electrically connected to a suitable high impedance amplifier such as a pH meter together with an ion measuring electrode in a manner well known in the art. Thus, the body of the electrode 10 is formed entirely of liquid junction material produced in accordance with the present invention. As a consequence, there is provided a very large surface area permitting ion diffusion so that clogging or plugging of the liquid junction structure is most improbable, particularly since ionic communication between the salt solution 18 and the sample requires only ion diffusion rather than liquid flow. Electrodes of this type may be readily machined and formed at little expense, requiring only a single material and no particular amount of skill. The electrode further has the advantage that, being formed of a polymeric material, it is not fracturable as is glass which is normally utilized as the material for the salt bridge tube of a reference electrode. Thus there is no danger of the electrode breaking in process streams. This advantage is of utmost importance in the pharmaceutical or food industries, as well as in medical and biological applications.

Electrodes formed of polymeric materials as to be hereinafter described embody all the advantageous characteristics of the invention except that the electrical resistance thereof may be what higher than is sometimes desired. In order to reduce this resistance, the lower end of the tube 12 may be machined relatively flat as indicated at phantom line 24 so as to provide a thin wall which will have lower resistance. For example, a container 12 having a wall thickness of about one-eighth inch may be machined at its lower end to provide a thin flat portion of about .060 inch thickness. Preferably, however, the resistance of the liquid junction structure is reduced by distributing a suitable salt, designated 26, throughout the polymeric material. This may be accomplished by mixing the salt with a suitable polymeric resin forming material, as will be hereinafter discussed, prior to molding and sintering the same to provide the polymeric bar stock used to form the electrode of the present invention.

Figure 2:
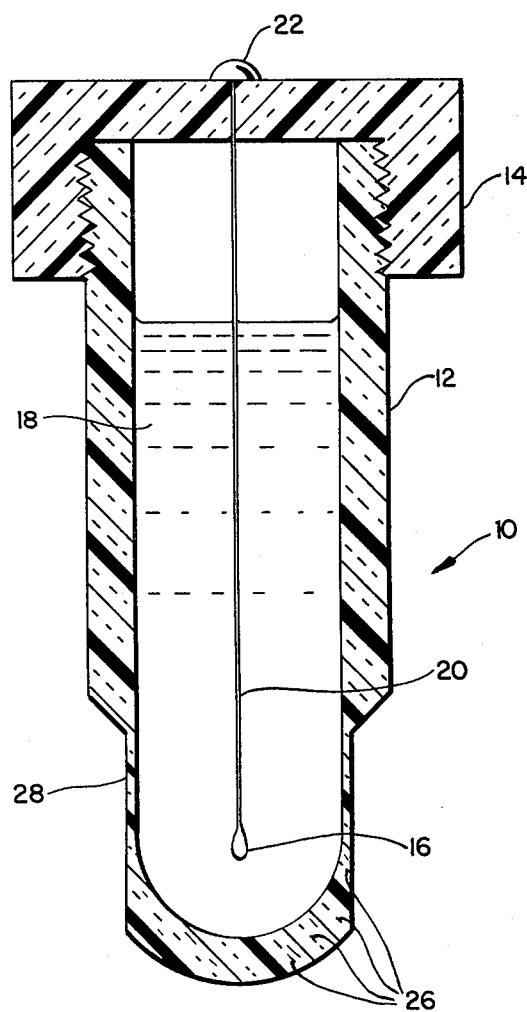
FIG. 2 illustrates an alternate form of the reference electrode of the instant invention in longitudinal section.

FIG. 2 shows an alternate construction. Here zone 28 of the sidewall of tube 12 has been reduced in thickness to about 0.035 to about 0.05 inches. The interstices of zone 28 may then be charged with electrolyte by internal pressurization, for example a pressure of greater than 150 psi. The interstices may also be charged simply by filling electrode 10 with electrolyte and letting it set for a period of time. In all cases the electrolyte will not run or seep through, even at zone 28. When electrode 10 is subsequently subjected to an external pressure greater than the internal, some of the interstices will collapse, locking in the charged electrolyte and there will be no flow of fluid from the outside to the inside.

In one form of the invention, the particulate material 26 comprises essentially inert particles. By the term "essentially inert", reference is made to materials that do not contaminate the salt bridge solution 18 or sample, and produce no spurious potentials, i.e., false, non-producible or unstable potentials, when contacted with samples having ionic strengths of the levels normally encountered. Thus, glass particles, for example, are considered to be essentially inert although, as will be explained later, glass in the liquid junction amy produce slight errors under certain circumstances.

There are presently available on the market various forms of hydrateable hydrophobic polymeric materials which have essentially inert particulate particles already incorporated therein and have been used by us to practice the invention. One such material is a nylon product which is designated by the plastics industry as Nylon 6/6 and contains molybdenum disulfide particles. Another suitable material is a nylon sold under the trade name Zytel. Another material which has been successfully utilized as a liquid junction structure is acrylonitrile-butadiene-styrene containing 40% by weight of glass fibers which are distributed throughout the plastic. It is of course understood that other forms of inert particulate material may be incorporated in the polymeric liquid junction of the present invention, for example, carbides of metals and non-metals, that is, tungsten carbide, silicon carbide, boron carbide; refractory silicates and silicate compositions including glass fibers, mica, asbestos, garnet, porcelain, zircon; metal oxides such as titanium oxide, zirconium oxide noble metals such as platinum, palladium and iridium as well as vitreous or crystalline materials, aluminates, etc.

As previously stated, it is preferred that the resistance of the liquid junction structure of the present invention be reduced by adding a suitable salt 26, preferably in the form of a powder, to the initial polymeric resin prior to the molding and sintering of the same into a bar stock. In this case, the salt comprises the particulate material 26. The salt should be electrochemically inactive in the sense that its presence per se in the polymer will not contaminate the salt bridge solution or internal half cell of the reference electrode. Relatively strong and water soluble salts are preferred, such as potassium chloride, sodium chloride and potassium nitrate, although obviously other salts could be utilized. It has been found, as will be shown later, that salt incorporated in the polymeric liquid junction structure of the present invention both lowers the junction resistance and tends to mask the effect of certain impurities which may be contained in the resin employed to form the polymeric structure. Of course, both the salt and essentially inert particles, such as glass, may be incorporated in the polymeric material.

In the preferred embodiment of the invention, the liquid junction structure is formed from hydrophobic polymers. Examples of such polymers are polyfluoroalkanes, polyethylene, polytetrafluoroethylene and polyvinyl chloride. Obviously other similar materials could be utilized. Such materials, being hydrophobic, do not normally permit ion diffusion therethrough. However, by incorporating the salts as discussed above therein, it has been found that these hydrophobic polymers permit ion diffusion therethrough, without liquid flow. Commercially available plastics of this type containing essentially inert particles which have been utilized successfully to practice the invention are polytetrafluoroethylene [Teflon] plastics containing glass fibers, namely TEC Fluorfil R and TEC Fluorfil BF3 manufactured by Thermech Engineering Corporation of Anaheim, Calif. In each case the particulate material is inert and does not adversely effect liquid junction structures formed from these plastic materials. The dye present is not required to practice the invention. These plastics contain about 15% by weight of glass fibers.

These commercial materials may be utilized as is in bar stock form and machined into reference electrodes of the configuration shown in the drawing or formed into discs which are sealed into suitable nonconductive tubes and thus provide liquid junction structures therefor. In the preferred embodiment, electrochemically inactive salts are incorporated, alone or together with the inert particles, in a hydrophobic polymeric resin at the time of the preparation of the polymer with the result that the liquid junction structure will have a relatively low electrical resistance.

We have further discovered that the purity of the polymer affects the potential of the reference electrode made therefrom. For example, we have found that if regular grade glass filled Teflon is utilized as the liquid junction structure of a reference electrode, the electrode exhibits appreciable deviation in the standard potential and the potential of the electrode is slightly dependent upon the iron concentration of the sample medium. The term "regular grade" Teflon refers to those Teflons wherein the resin and glass fibers are passed through iron or steel screens in processing. It is believed that in the passage of these materials through the screens iron is picked up on the resin particles and glass fibers passing therethrough. This is apparent from the slightly pinkish color of the resulting polymer formed from this mixture. In contrast, we have found that when a reference electrode has a liquid junction structure formed of "chrome screened" glass filled Teflon, the electrode does not exhibit any appreciable deviation in the standard potential and the potential of the electrode is insensitive to the ion concentration of the sample. The term chrome screened in the plastics art refers to a process in which Teflon resin particles and glass fibers are passed through a chrome plated screen with the result the polymer molded therefrom is white rather than pink, thus exhibiting an absence of metallic impurities therein.

The practicality of the present invention, the effect of the absence of impurities in glass filled Teflon, and the effect of the addition of a salt to a glass filled Teflon liquid junction structure, can best be appreciated by making reference to the following table:

TABLE I

| Buffer | Fiber | Pink Teflon | White Teflon | Pink Teflon Incorporating Salt (5%) | White Teflon Incorporating Salt (5%) |
|---|---|---|---|---|---|
| 4.01 | 4.06 | 4.1 | 4.02 | 4.1 | 4.0 |
| 7.0 | 7.0 | 7.0 | 7.0 | 7.0 | 7.0 |
| 9.18 | 9.1 | 8.95 | 9.05 | 8.95 | 9.11 |

TABLE I-continued

| Buffer | Fiber | Pink Teflon | White Teflon | Pink Teflon Incorporating Salt (5%) | White Teflon Incorporating Salt (5%) |
|---|---|---|---|---|---|
| 10.0 | 9.8 | 9.73 | 9.86 | 9.9 | 9.94 |

The first column headed "Buffer" in Table I above indicates the pH of four standard buffer solutions which were utilized as test solutions in which five different reference electrodes were compared. The second column headed "Fiber" lists pH readings made with a standard reference electrode incorporating an asbestos fiber liquid junction. The third column headed "Pink Teflon" lists pH readings made with a reference electrode having a liquid junction structure formed of a regular grade glass filled Teflon, which contains metallic impurities as evidenced by its pink color. The fourth column headed "White Teflon" lists pH readings made with a reference electrode having a junction formed of chrome screened glass filled Teflon which contains no iron impurities. The fifth column headed "Pink Teflon Incorporating Salt (5%)" lists pH measurements made with a reference electrode having a junction formed of regular grade glass filled Teflon in which 5% by weight of potassium chloride was incorporated. The last column headed "White Teflon Incorporating Salt (5%)" lists pH readings made with reference electrode having a liquid junction structure formed of chrome screened glass filled Teflon in which 5% by weight of potassium chloride was incorporated. In each case, the pH readings were made with the reference electrode being tested and a conventional glass pH electrode both connected to a pH meter.

As will be seen by comparing the various pH readings in the table, electrodes incorporating our liquid junctions compare favorably with the conventional electrode incorporating as asbestos fiber junction. The pH readings in the table further show that there is generally less deviation from the true pH value of the buffer utilizing the white Teflon junctions than the pink Teflon junctions with or without salt, and the pink Teflon junction incorporating the salt shows less deviation and greater span in the pH readings than the pink Teflon junction not containing a salt. The data indicate that the provision of salt in the glass filled Teflon liquid junction structure both lowers the junction resistance and masks the effect of iron contained in the regular grade glass filled Teflon. It is seen that the greatest span of pH readings and least amount of deviation from the true pH are provided with the white glass filled Teflon junction incorporating a salt.

The amount of inert particles and of salt utilized in any of the liquid junction structures of the invention does not appear to be critical. For example, we have successfully made Teflon liquid junction structures containing from 15 to 25% by weight of glass fibers as compared to the weight of the resin, without any noticeable difference in the ion potential measurements of reference electrodes embodying such structures. Also we have utilized from 5 to 30% by weight, as compared to the Teflon-glass mixture, of potassium chloride salt with no noticeable difference in the electrochemical characteristics of the junction. However, when the amount of salt exceeds 30%, the durability and structural rigidity of Teflon is impaired somewhat. Obviously the amount of the inert particles and salt which may be added to the polymer will depend upon the nature of the polymer itself, and of the inert particles and salt.

The preferred method of making liquid junction structures of non-hydrateable hydrophobic polymers is as follows. The polymeric resin particles, preferably Teflon in the form of filaments having an average length of 35 microns (Teflon T-7), are passed preferably through a chrome screen. To this there is added a desired amount of the appropriate salt having particle sizes of 10 to 1000 microns. These materials are then mixed in a suitable blending apparatus and molded for example into bar stocks or sheets. After the blending step, the particles have a particle size from about $1 \times 10^{-4}$ to about $50 \times 10^{-4}$ centimeters. The salt particles are coated with a filamentary structure of Teflon which prevents leaching of the particles in use. The molding pressure is from 2,000 to 10,000 pounds per square inch, depending upon properties desired. The molding may be achieved either by compression or extrusion and is followed by sintering at a suitably high temperature in a manner well known in the plastics art. The temperature will of course depend on the particular resin being utilized. After the bar stock has been formed, it is preferably machined into a reference electrode body as shown in the drawing so that the entire body is formed of a liquid junction material. It has been found that the thickness of the wall of the salt bridge tube does not appreciably affect the electrochemical characteristics of the electrode. Electrodes of this type having a wall thickness of about one-eighth inch have been found to have junction resistances as low as 200 ohms. In addition, all of the electrodes of the present invention can withstand pressures of liquid samples as high as 300 psi without external attachments to the electrodes for internal pressurization of the salt bridge solution. Since the entire bodies of the electrodes are formed of liquid junction material, they do not present any clogging problems from viscous samples. The electrodes also as not adversely affected by stirring or flow rates of most samples and do not exhibit any leakage of salt bridge solutions over periods of several months, thus establishing that ionic communication is provided by means of diffusion of ions rather than liquid flow.

Reference electrodes having liquid junctions made out of the glass filled materials discussed above with added salts, are entirely suitable for measuring the pH of samples having typical ionic strengths. However, they exhibit an ionic sensitivity effect in measuring the pH of liquids having an ionic strength less than $100\mu$ Mhos (reciprocal ohms — a unit of conductivity) such as is encountered in high purity water. This could be caused by the glass fibers acting as capillaries and acting as hydrogen ion sensors as in the familiar pH glass electrode. Further, the presence of the glass fibers give rise to the so-called streaming potentials that are dependent upon the ionic strength of such test media. These drawbacks can be minimized by making the liquid junction structure out of glass-free polymeric materials, such as Teflon with inert particles other than glass, and containing an appropriate amount of electrochemically inactive salt. We have found that liquid junction structures of this type satisfy all of the above mentioned criteria and have the added advantages in that pH measurements are not influenced even in samples having ionic strengths at levels less than $100\mu$ Mhos and are relatively insensitive to the flow rates of such samples. In additon, this type of liquid junction structure produces results in standard pH buffer solutions at least as favorable as that of any of the other structures described above. For example, a reference electrode having a liquid junction structure formed of white Teflon free of glass particles and incorporating 20% by weight potassium chloride when tested with a conventional pH glass electrode in the buffer solutions listed in Table I above produced the following readings: 4.01, 7.0, 9.18 and 9.98.

In order to understand the significant differences between the new reference electrode and a conventional reference electrode, it will be helpful to review briefly the operation of a reference electrode as generally understood. Examples of conventional reference electrodes are mercury-calomel and silver-silver chloride. The supporting electrolyte in either of these electrodes is potassium chloride, the chloride ion being responsible for determining the potential of the electrode. The salt bridge was developed so that the electrode can be used in solutions other than potassium chloride. The generally used electrolyte comprises potassium chloride, except when the chloride ion is not desirable. Potassium chloride is most commonly used because of the near equitransference of anion and cation. This equitransference salt is alleged to minimize the so called junction potentials encountered in electrochemical measurements with reference and measuring electrodes. In general practice liquid junction potentials as high as 40 mv are encountered which renders suspect this feature of the equitransference salt.

All pH systems are characterized by the presence of $H_2O$ or $H^+$ and $OH^-$ ions. Therefore it appeared that these species are responsible for the performance of glass (pH) or reference electrodes. Accordingly, an electrode body (junction) which would permit the diffusion of the above species and not act as a capillary was made. This consisted of a nylon (6/6) rod with about an 0.030 inch thick section at the end. A section of about 0.030 inch nylon was found to contain the aqueous solution inside without flow through. When subjected to external pressure in a hydrostatic system no flow of external liquid surrounding the electrode into the body was observed. Yet this body worked as a junction when a reference electrode was construed in the usual manner. This proves that the flow or migration of potassium chloride (KCl) is not necessary for a material to be useful in constructing a reference electrode junction. Moreover this type of reference electrode did not exhibit excessively large junction potentials as would be expected if it is necessary for $K^+$ $Cl^-$ ions to flow through the junction path. From these experiments it, therefore, appears that a semipermeable membrane for $H_2O$, $H^+$, $OH^-$ species will perform as a reference electrode junction. However, nylon is not always a suitable material for use in varied process applications. Teflon is the best inert plastic known. Teflon is also known to be hydrophobic. In order to make it act as a diffusion membrane, several compositions of Teflon with other filling materials such as glass fibers, and inert salts such as $KNO_3$ and KCl were tried. All these showed the promise of being useful in the construction of a reference electrode which would function primarily as a semipermeable membrane and not as a capillary junction as is the case with conventional reference electrodes.

Figure 3:
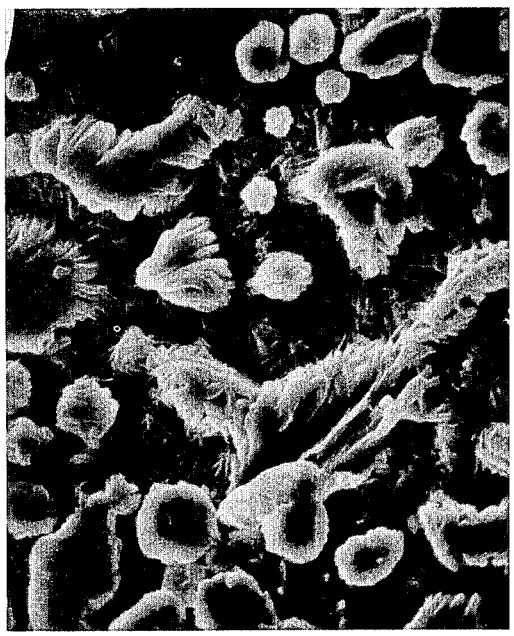
FIG. 3 is an electron photomicrograph of electrode material according to the instant invention.

FIG. 3 is an enlargement (at 2000× magnification) of a section of electrode material made in accordance with the instant invention. The enlargement was made by a scanning electron microscope. The material contained 20% KCl powder and the balance was Teflon T-7. The interstitial spacing and filamentary coating of some of the salt particles may be plainly seen.

Figure 4:
FIG. 4 is an electron photomicrograph of electrode material according to the instant invention.

FIG. 4 is a further enlargement of a portion of FIG. 3 at 6000×.

Figure 5:
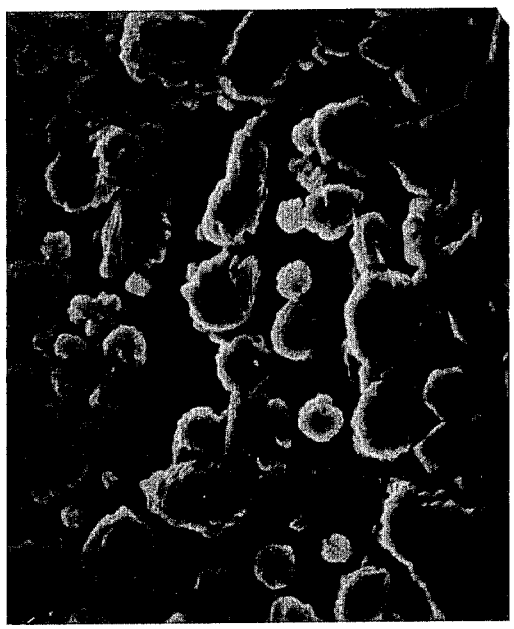
FIG. 5 is an electron photomicrograph of electrode material according to the instant invention.
Figure 6:
FIG. 6 is an electron photomicrograph of electrode material according to the instant invention.

FIGS. 5 and 6 are similar to FIGS. 3 and 4 respectively. The difference is that the FIGS. 3 and 4 material was molded at 6000 psi and the FIGS. 5 and 6 material was molded at 4500 psi. The lower pressure molded material had a lower electrical resistance in operation as an electrode.

Figure 7:
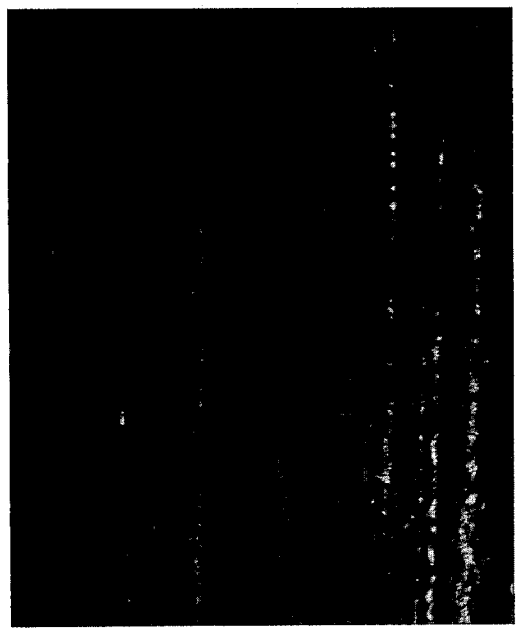
FIG. 7 is an electron photomicrograph of a polytetraflouroethylene membrane.

FIG. 7 is an enlargement (10,000×) of a section of a plain Teflon membrane. The lack of interstices and filaments is apparent. What appear to be slight cracks on the surface are a result of the preparation for the electron micrograph.

Figure 8:
FIG. 8 is an electron photomicrograph of electrode material according to the instant invention.

FIG. 8, by comparison, is a further enlargement (10,000×) of the FIGS. 5 and 6 material. The interstices and filamentary wrapping are apparent.

It is worthwhile to examine the current views on permeation of liquids/vapors in the plastic membranes. Alexander Lebovits reviewed the permeability of polymers to gases, vapors and liquids [Modern Plastics 139 (1966)]. Mass transport through polymers in contrast to transport through filter paper or other porous materials (Knudsen flow or Poiseuille flow) occurs by activated diffusion. Activated diffusion is believed to involve three steps:

(i) dissolution of the permeant in the membrane on the side of its higher concentration; (ii) diffusion through the membrane towards the side of its higher concentration, a process which depends upon the formation of "holes" in plastic network due to the thermal agitation of the chain segments; and (iii) desorption of the permeant on the side of lower concentration. These processes are not contemplated in the diffusion through porous materials. Other important differences exist with regard to temperature and hydrostatic pressure dependence. While exact data are not available yet all the operational characteristics of the new reference electrode lead to the conclusion that this must be based upon activated diffusion phenomenon.

Any water permeable membrane should be useful in constructing a reference electrode. However, if the material is hydrophilic and has functional groups or chain segments chemically similar to the penetrant, such as cellophane and water, the cohesive forces between the polymer and the vapor are large. As a result the solubility of permeant and so the transport in the membrane is greatly increased. If the permeant is dissimilar to the membrane material such as Teflon, polyethylene and others the permeation of water is greatly reduced. Indeed these materials as such do not function as useful materials for the construction of reference electrodes; until they are made hydrophilic by creating holes for the permeation of water. This is accomplished as described above. An alternate mechanism for the permeation of water in these materials is conceivable. According to this the inert material (e.g., $K^+$ in KCl) could form aquocomplexes which would serve as exchange sites for $H_2O$ and thus function as a semipermeable membrane (governed by activated diffusion phenomenon). The function of a reference electrode in electrochemical measurements consists in providing a constant potential. The means of establishing electrical continuity is what gave rise in the past to the disadvantages of the currently known electrodes.

Summarizing briefly, the following are some basic experimental observations of the new reference electrode:

a. the electrode is usable in any system aqueous or non-aqueous.
b. the electrode does not require external pressurization.
c. the temperature coefficient is close to that of the internal element instead of being an ambiguous quantity.
d. the electrode has no significant liquid junction potentials. This was determined by using the electrode in solutions of varying ionic strength and charge.
e. there is no noticeable transport of ions such as sulfide or chromate or copper or lead, etc. from an external medium into the body of the electrolyte (internal filling solution).
f. there is no noticeable transport of either $K^+$ or $Cl^-$ or $Ag^+$ from the internal solution to the external medium in several months of operation.
g. the existence of the postulated holes results in an extremely conductive membrane. The typical resistance of the junction in aqueous solutions is of the order of 1000 to 1,000,000 ohms as opposed to $10^{14}$ to $10^{17}$ ohm for pure polyethylene and Teflon.

All these and probably some other observations with this electrode are possible because there is no appreciable change in the concentration of the active species such as $H_2O$, $H^+$, $OH^-$ from inside of the electrode body to the outside.

Although we have herein shown and described our invention in what we have construed to be the most practical and preferred embodiment, it is recognized that departures may be made therefrom within the scope of our invention, which is not to be limited to the details disclosed herein but is to be accorded the full scope of the claims so as to embrace any and all equivalent structures, methods and devices.

What is claimed is:

1. An electrochemical reference electrode comprising:
    an electrode body of liquid impermeable polymeric material, said electrode body forming a closed internal chamber;
    a water soluble salt selected from the group consisting of potassium chloride, sodium chloride, and potassium nitrate distributed through at least a portion of said liquid impermeable polymeric material to form a liquid junction structure in said electrode body, at least some of said water soluble salt being in particulate form and being held in place by a filamentary coating of said polymeric material;
    an internal half cell disposed in said chamber;
    means for making an electrical connection to said internal half cell; and,
    an internal filling solution in said internal chamber;
    said electrode having no path for leakage of a test solution into said internal chamber or for leakage of said internal filling solution into a test solution when said electrode is immersed in a test solution.

2. An electrochemical reference electrode as claimed in claim 1 wherein:
    the polymeric material is polytetrafluoroethylene;
    said water soluble salt is about 5 to about 30% by weight; and,
    said particles are from about 10 to about 1,000 microns in size.

3. An electrochemical reference electrode as claimed in claim 2 wherein the polytetrafluoroethylene used to form said liquid junction is in the form of filaments having an average length of about 35 microns.

4. An electrochemical reference electrode as claimed in claim 1 wherein additionally:
    said liquid impermeable polymeric material has glass fibers distributed throughout.

* * * * *